United States Patent [19]
Arkell et al.

[11] Patent Number: 4,578,078
[45] Date of Patent: Mar. 25, 1986

[54] INTRAOCULAR LENS WITH ASYMETRIC VAULTED SUPPORT LOOPS

[75] Inventors: James J. Arkell, Lake Elmo; Robert N. Hamlin, Stillwater, both of Minn.

[73] Assignee: Minnesota Mining and Manufacturing Company, Saint Paul, Minn.

[21] Appl. No.: 364,396

[22] Filed: Apr. 2, 1982

[51] Int. Cl.⁴ .............................................. A61F 2/16
[52] U.S. Cl. ........................................................ 623/6
[58] Field of Search ................................................ 3/13

[56] References Cited

U.S. PATENT DOCUMENTS

| | | | |
|---|---|---|---|
| 2,834,023 | 5/1958 | Lieb | 3/13 |
| 3,866,249 | 2/1975 | Flom | 3/13 |
| 3,913,148 | 10/1975 | Potthast | 3/13 |
| 3,994,027 | 11/1976 | Jensen et al. | 3/13 |
| 4,014,049 | 3/1977 | Richards et al. | 3/13 |
| 4,073,015 | 2/1978 | Peyman et al. | 3/13 |
| 4,092,743 | 6/1978 | Kelman | 3/13 |
| 4,110,848 | 9/1978 | Jensen | 3/13 |
| 4,134,160 | 1/1979 | Bayers | 3/13 |
| 4,134,161 | 1/1979 | Bayers | 3/13 |
| 4,159,546 | 7/1979 | Shearing | 3/13 |
| 4,174,543 | 11/1979 | Kelman | 3/13 |
| 4,198,714 | 4/1980 | Jensen | 3/13 |
| 4,249,271 | 2/1981 | Poler | 3/13 |
| 4,328,595 | 5/1982 | Sheets | 3/13 |

FOREIGN PATENT DOCUMENTS 0032835 7/1981 European Pat. Off. ............... 3/13

OTHER PUBLICATIONS

Model PC-11 Posterior Chamber, American Medical Optics, American Hospital Supply Corp., advertisement brochure, Aug. 1981.
1981 Publication of Surgidev Corporation entitled "The Leiske ™ Physioflex ™ Style 10 Anterior Chamber Lens".
The publication of McGhan/3M entitled "Anterior Chamber Liteflex ™ Style 70 Intraocular Lens".

*Primary Examiner*—Ronald L. Frinks
*Attorney, Agent, or Firm*—Donald M. Sell; James A. Smith; Jennie G. Boeder

[57] ABSTRACT

An intraocular lens assembly suitable for implantation into either the anterior or posterior chamber of the human eye has a lens body supported in the eye by first and second support members extending from the lens body for engaging adjacent portions of the anterior or posterior chamber of the eye, at least one of the support members comprising an asymmetric spring-like support loop of circular cross-section extending outwardly from the peripheral edge of the lens body; the support loop has first and second leg portions attached to the periphery of the lens body diverging outwardly from the lens body, each leg portion containing a sloped portion with the sloped portion of each leg being of nearly equal lengths; the outer edge of the support loop is received in and biased against the natural cavities and angles of the eye from which the natural lens has been removed and has one or more contact portions for engaging the adjacent portions of the eye.

14 Claims, 10 Drawing Figures

INTRAOCULAR LENS WITH ASYMETRIC VAULTED SUPPORT LOOPS

This invention relates to an intraocular lens suitable for use as an artificial lens implant in either the anterior or posterior chamber of the human eye. Particularly, this invention relates to an intraocular lens having at least one asymmetric resilient spring-like support loop which contains sloped portions of near equal length which provide the lens with a vault, and outer contact portions for holding the lens in place in the eye.

Intraocular lens implantation after cataract surgery has come into common usage because of the improved vision obtained thereby over the alternatives of contact lenses or spectacles. Intraocular lenses have been implanted in both the posterior as well as the anterior chambers of the eye. In general format, an intraocular lens consists of a lens body and a plurality of support members usually projecting from different sides of the lens body for use in supporting the lens in position in the eye. Within the basic format, however, several different designs of intraocular lenses are currently available. In most of these, the position fixation elements or support means are in the form of rigid loops, arms, plates, legs and the like, such as exemplified by the rigid loops 12 and 13 in Jensen, U.S. Pat. No. 4,110,848, and by the rigid plates 12 and 13 of Kelman, U.S. Pat. No. 4,092,743. Both the Jensen and the Kelman patents disclose rigid loops or plates which extend through the iris. Prongs extending through the iris are disclosed as fixation means in the Flom, U.S. Pat. No. 3,866,249. Jensen, U.S. Pat. No. 3,994,027 and Peyman, U.S. Pat. No. 4,073,015, both disclose rigid support loops engaging the anterior capsule wall.

A recent more flexible posterior chamber lens is disclosed by Shearing, U.S. Pat. No. 4,159,546 in which J-shaped elastic support members extend outwardly from opposite peripheral edges of the lens to engage the ciliary body, or possibly the lens capsule, to support the lens in position.

It has also been proposed by Grinder in U.S. Ser. No. 113,682, to employ flexible capsule engaging support loops of a shape similar to element 12 of the Kelman Patent, U.S. Pat. No. 4,092,743 with two of such loops extending from opposite sides of the lens body. Additionally, Sheets, in U.S. Ser. No. 71,375, employs flexible support loops for engagement with the lens capsule.

Furthermore, it is known to fashion the support members of the lens so that they have sloped or inclined portions which result in the portions of the support members which are to contact the eye being non-planar with the lens body. Such lenses are said to be "vaulted" and are disclosed in, for example, U.S. Pat. Nos. 2,834,023; 4,092,743; 4,110,848; and 4,134,161.

Notwithstanding the great strides made in lens implantation, as evidenced by the thousands of successful lens implantations, complications in individual cases continue to arise in a small percentage of the cases. For example, the lenses of the prior art are relatively unstable and are easily mispositioned which may cause them to come in contact with the cornea, or iris thereby causing cell death or erosion of these parts of the eye. Improper sizing and excessive weight of the lens and support elements also cause subsequent mispositioning of the lens in some instances. Additionally, the use of sutures and other similar connectors engaging viable portions of the eye may cause cell death or erosion of these parts of the eye.

This invention provides an improved and more stable intraocular lens for positioning in either the anterior or posterior chamber of the eye. The lens of this invention is easy to implant and has stability without suturing.

The lens of the present invention comprises a lens body; first and second support members extending from the lens body for engaging adjacent portions of the anterior or posterior chamber of the eye, at least one of the support members comprising a resilient spring-like asymmetric support loop extending outwardly from the periphery of the lens body, this support loop having first and second end portions attached to the lens body at first and second attachment locations extending chordally with respect to said lens body, first and second legs extending from said first and second end portions, respectively, each of said leg portions containing at least a portion which is sloped relative to a plane perpendicular to the axis of the lens body, with the sloped portion of the first leg being nearly equal in length to the sloped portion of the second leg; and a transverse portion with opposite sides being respectively unitarily connected to the first and second legs and including one or more outer contact portions dimensioned and shaped to engage adjacent portions of the anterior or posterior chambers with an outward radial force when positioned therein so that at least one of the outer contact portions is deflected inwardly from the normal relaxed position by the adjacent portion of the eye to provide support for the lens body, said transverse portion positioned in a plane which is spaced apart from but substantially parallel to the plane of the lens body. The support members extend outwardly in a symmetrical manner from generally opposite sides of the periphery of the lens body. The asymmetric support loop is generally foot-shaped, and the sloped portions of the leg portions provide the lens with a vault.

Due to the particular construction of the asymmetric support loop of the lens, that is, the inclusion of first and second legs having sloped portions of near equal length, the lens of the present invention is highly flexible and highly stable, with a reduced tendency to become mispositioned when implanted in the eye. The lens is designed for easy and essentially automatic and accurate positioning within either the anterior or posterior chambers of the eye, preferably, within the posterior chamber. The lens is vertically, horizontally and rotationally secured by the spring action of the support loops in contact with the adjacent portions of the eye. There is normally no need for suturing of the support means to any portion of the eye, and when the lens is placed in the eye, there is ordinarily an absence of contact with the cornea and iris. Thus, there is an attendant absence of problems which can be caused by lenses which come in contact with these portions of the eye.

The invention will now be described in more detail with reference to the following drawings in which like reference numerals are used for the same parts as shown in different figures.

Figure 1:
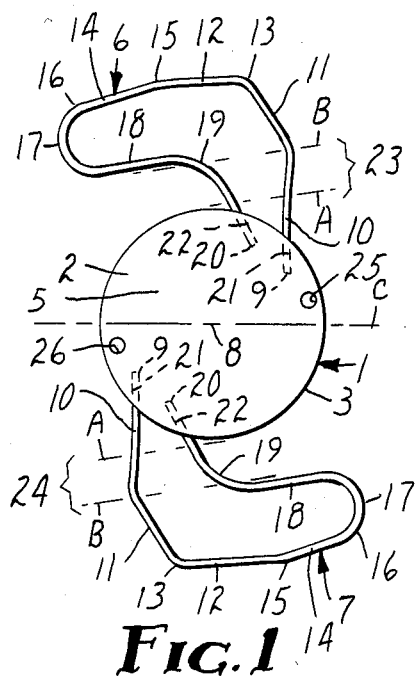
FIG. 1 is a front elevation view of the preferred embodiment of the invention.
Figure 2:
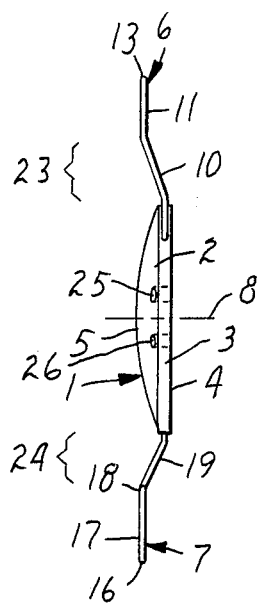
FIG. 2 is a side elevation view of the preferred embodiment.

Referring now to FIGS. 1 and 2, the lens 1 comprises a lens body 2 having cylindrical peripheral surface 3, planar surface 4, and spherical surface 5. The lens body 2 is normally four to six millimeters in diameter and is made by molding or lathing of optical polymeric material such as polymethyl methacrylate. The spherical surface 5 is of a desired curvature to give the required optical characteristics for the particular patient in which the lens is to be implanted. Apertures 25 and 26 are provided in the lens for permitting receipt of the ends of an instrument or tool for holding and positioning the lens during and after insertion in the eye.

The lens body 2 is held in place in the eye by means of two identical support loops 6 and 7. These support loops are made of a resilient spring-like material such as polypropylene. Other materials having similar resiliancy characteristics can be used if they are inert and substantially nonreactive in the human body. Preferably the loops are formed so as to have a circular cross-section of about 0.10 to 0.30 mm in diameter, preferably about 0.15 mm in diameter.

The support loops 6 and 7 have identical asymmetric foot-like configurations with the ankle portion of each foot being attached to the lens body 2. Loops 6 and 7 are generally symmetrical with the optical as well as the geometric axis 8 of the lens body 2. In the relaxed condition of the lens 1, as shown in FIG. 1, the outermost portions of the respective loops are preferably about 14 millimeters apart if the lens is to be placed in the ciliary sulcus. If the lens is to be positioned in the capsular bag, it is preferred that the loops be about 13 mm apart.

Each loop contains a first linear end portion 9 embeddedly attached in a chordal bore in the lens body 2 and extending outwardly to a first leg having first leg portion 10 which contains a first sloped leg portion between imaginary lines A and B. First leg portion 10 leads to second leg portion 11. Both first leg portion 10 and second leg portion 11 are preferably of linear configurations. Second leg portion 11 meets first leg portion 10 at an angle which is less than about 180 degrees. Second leg portion 11 leads to first transverse portion 12. Second leg portion 11 and transverse portion 12 meet at an angle which is less than about 180 degrees. At the intersection of second leg portion 11 and first transverse portion 12 lies first contact portion 13 which is to contact the ciliary sulcus when the lens is positioned in the posterior chamber, or the anterior angle when the lens is positioned in the anterior chamber. First transverse portion 12 is further connected to second transverse portion 14. First transverse portion 12 and second transverse portion 14 are also preferably of linear configuration. First transverse portion 12 and second transverse portion 14 also meet at an angle which is less than about 180 degrees. At the intersection of first transverse portion 12 and second transverse portion 14 lies second contact portion 15. It should be observed that transverse portions 12 and 14 are positioned in a plane which is perpendicular to the geometric axis 8 of the lens body 2 and is substantially parallel to the posterior surface 4 of the lens body 2. Second transverse portion 14 is in turn connected to a second leg at third contact portion 16. The second leg connects the transverse portions of the loop, 12 and 14, back to the lens body 2. The second leg forms a smooth S curve and comprises three portions: a first portion 17 which begins at contact portion 16 and is approximately 180 degrees in curvature; a second portion 18 which has a curvature of about 0 degrees; and a third portion 19 which is curved in a direction opposite to portion 17 and is less than about 180 degrees in curvature. Third portion 19 of the second leg contains a second sloped portion lying between imaginary lines A and B. It should be observed that the length of the sloped portion of first leg portion 10 is nearly equal to the length of the sloped portion of second leg portion 19.

Second leg portion 19 is embeddedly attached in a chordal bore in lens body 2 at second linear end portion 20. First and second linear end portions 9 and 20 are respectively embeddedly attached to the lens body 2 at chordal holes 21 and 22 in lens body 2. End portions 9 and 20 are chordally positioned inside the lens body 2 and bonded thereto by a heat probe, ultrasonic probe, or adhesive probe in a conventional manner. Alternatively, lens body 2 and loops 6 and 7 can be molded unitarily.

Lens body 2 contains two holes 25 and 26 which pass through the body of the lens and are located in close proximity to the peripheral edge 3 of the lens body 2. Preferably, holes 25 and 26 are about 0.5 mm in diameter and are located about 0.5 mm from the peripheral edge 3 of the lens body. These holes are not a required feature of the lens of the invention but are preferably provided in order that the surgeon may rotate the lens during surgical that the surgeon may rotate the lens during surgical implantation by established surgical techniques.

While it is preferred, as shown in FIG. 1 that the loops provide three point contact with the eye by the use of three contact portions 13, 15 and 16 contained within transverse portions 12 and 14 of the loop, it is also contemplated that the transverse portions of the lens may provide more than three contact points or less than three contact points. Alternatively the transverse portions 12 and 14 of the loop may be combined to form a smooth continuous curve which is designed to be substantially equivalent to that of the outer portion of the posterior chamber of the eye, or preferably the equator of the ciliary sulcus so that when the loops 6 and 7 are compressed within the posterior chamber or lens capsule the transverse curved portion of loops 6 and 7 follow the outer portion of the posterior chamber or the equator of the ciliary sulcus. Since the posterior chamber and lens capsule vary from one patient to the other, often this curve will not track that of the posterior chamber or equator. In some cases, only a portion of the curved transverse portion will contact the posterior chamber outer portion or equator of the ciliary sulcus.

It should be observed that third contact portion 16 is positioned radially outwardly a greater distance from the lens body 2 than are first and second contact portions 13 and 15. Inward movement of third contact portion 16 as a result of positioning of the loops 6 and 7 in the posterior chamber as in FIG. 4 brings portion 17 of the second leg into closer proximity with the lens body 2 than is the case when the loops are in the relaxed condition of FIG. 1.

It should be observed that first leg portion 10 and second leg portion 19 diverge outwardly from the lens body 2. Leg portion 10 has the configuration of a columnar support while leg portion 19 has the configuration of a cantilever support. The locations of the inner ends of leg portions 10 and 19 are such that the chords formed by an imaginary extention of these leg members are separated by approximately 27 degrees.

An essential feature of the lenses of this application is the placement of a vault or sloped portion in the support loops. Referring now to FIGS. 1 and 2, both the first and second legs of loops 6 and 7 contain identical sloped portions 23 and 24 lying between imaginary lines A and B which are inclined somewhat anteriorly to lens body 2. As a result of this incline, the first and second transverse portions 12 and 14 of both loops 6 and 7 lie in a common plane which is parallel to the posterior surface 4 of the lens body 2. Sloped portions 23 and 24 have the same degree of inclination such that the transverse portions 12 and 14 of loop 7 lie substantially in the same plane with the transverse portions of loop 6. The degree of the inclination of sloped portions 23 and 24 is such that the perpendicular distance from the plane of the transverse portions 12 and 14 to the posterior surface 4 of the lens body is between about 1.5 and 0.1 mm, preferably between about 1.0 and 0.3 mm, and most preferably about 0.6 mm. Preferably sloped portions 23 and 24 form an angle with the planar surface 4 of the lens body 2 of between about 5 and 90 degrees, more preferably between about 20 and 30 degrees, and most preferably about 25 degrees.

Referring back to FIG. 1, the portions of loops 6 and 7 which comprise sloped portions 23 and 24, respectively, are shown lying between two parallel imaginary lines A and B. Imaginary lines A and B are drawn so that they lie in a non-parallel relationship to imaginary line C. Imaginary line C is drawn so that it is perpendicular to columnar leg portion 10 and intersects and is perpendicular to the geometric axis 8 of the lens body 2. Additionally, imaginary lines A and B are drawn so as to provide that the sloped segments lying between lines A and B on both the first and second legs, are nearly equal in length. By nearly equal in length it is meant that the sloped portions of the first and second legs differ in length by no more than about 35%, preferably by no more than 20% and most preferably by no more than about 1%. It has been found that the inclusion of sloped portions 23 and 24 in the support loops provides a lens having improved stability and improved resistance to rotational and vertical movement of the lens body when implanted in the eye.

It is preferred that lines A and B be parallel to a line drawn tangential to second portion 18 of the second leg. The length of the first and second legs which comprise the sloped portions is preferably the distance from as close to the lens periphery 3 as possible, without touching the periphery of the lens, to, but not touching, portion 18 of the second leg. Preferably the length of the sloped portions is between about 0.3 and 3 mm, most preferably about 1.5 mm.

Figure 3:
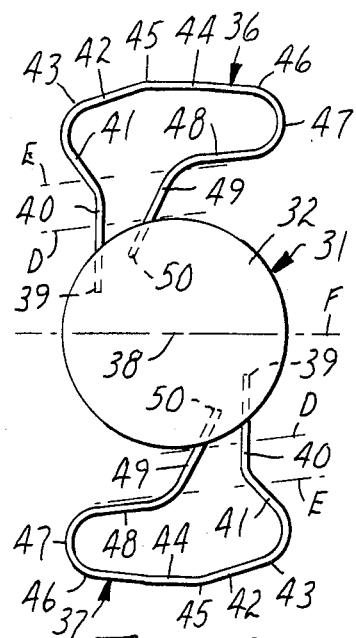
FIG. 3 is a front elevation view of an alternative embodiment of the invention.

It is also contemplated, in accordance with another embodiment of the present invention, to provide an intraocular lens which has the structure depicted in FIG. 3. As shown in FIG. 3 the lens 31 includes a lens body 32, and first and second identical asymmetric support loops 36 and 37. The support loop 37 has a first linear end portion 39 embeddedly attached to the lens body 32 and leading to a first leg which comprises a linear first portion 40 and a second portion 41 which is of an arcuate configuration. Support loop 37 resembles a foot wherein the second arcuate portion 41 is the heel of the foot. second arcuate portion 41 begins by curving outwardly away from first portion 40 at an angle which is greater than 180 degrees. Second portion 41 then curves inwardly towards transverse portion 42 and meets portion 42 at an angle which is less than 180 degrees in curvature. Transverse portion 42 leads to transverse portion 44 and meets transverse portion 44 at an angle less than 180 degrees. Contact portions 43, 45 and 46 lie along transverse portions 42 and 44 and are used to hold the lens in place when implanted in the eye. Transverse portion 44 leads to a second leg which forms a smooth S curve and comprises three portions: a first portion 47 which begins at contact portion 46 and is approximately 180 degrees in curvature; a second portion 48 which has a curvature of about 0 degrees; and a third portion 49 which is curved in a direction opposite to portion 47 and is less than about 180 degrees in curvature. Second leg portion 49 is attached to the lens body 32 at second linear end portion 50.

The first and second legs of loop 37 contain sloped portions in first leg portions 40 and 41 and in second leg portion 49 which are positioned between imaginary parallel lines D and E. These sloped portions are inclined somewhat anteriorly to lens body 32, such that transverse portions 42 and 44 are positioned in a common plane which is perpendicular to the geometric axis 38 of the lens body 32 and is substantially parallel to the posterior surface of the lens body 32. Imaginary lines D and E are non-parallel to imaginary line F which is drawn so that it is perpendicular to first leg portion 40 and intersects and is perpendicular to the geometric axis 38 of the lens body 32. Imaginary lines D and E are similar to imaginary lines A and B and preferably have approximately the same location in the loop 37 as lines A and B have in loop 7.

Figure 4:
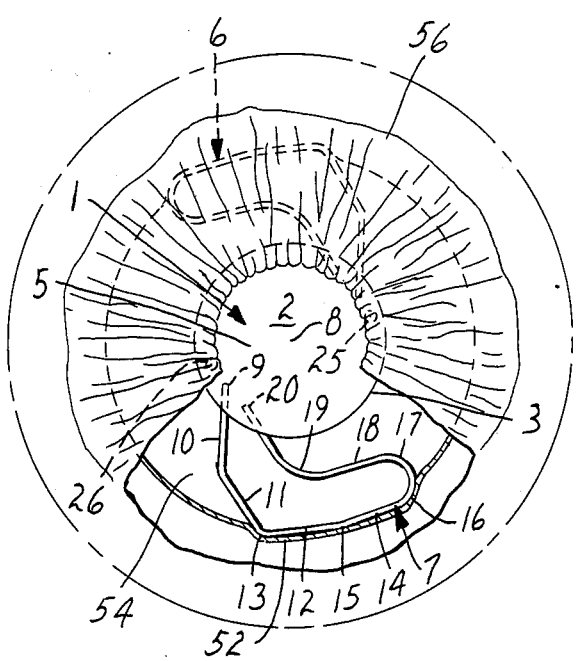
FIG. 4 is a front elevation view of the preferred embodiment of the invention as implanted in the posterior chamber of the eye, less portions removed for clarity.
Figure 5:
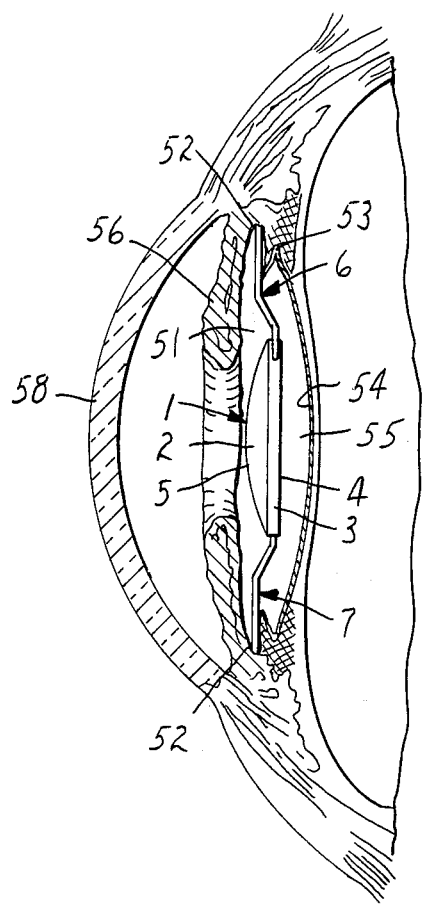
FIG. 5 is a bisected sectional view of the eye of FIG. 4 with the lens in the posterior implanted position.

In use the intraocular lens 1 is preferably placed within the posterior chamber of the eye after the natural lens has been removed from the lens capsule by normal extracapsular cataract removal. Referring to FIGS. 4 and 5, the central portion 51 of the lens capsule anterior surface is removed along with the natural lens. This leaves the ciliary sulcus 52, equatorial region 53 and posterior wall 54 of the lens capsule in the position shown in FIG. 5.

The lens 1 is positioned within the ciliary sulcus 52 by compression of loops 6 and 7. This compression causes loops 6 and 7 to move cylindrically around the lens body 2 and towards the lens body 2. First leg portions 10 and 11 and second leg portions 18 and 19 become closer in proximity during the compression. Additionally, transverse portions 12 and 14 and the periphery of the lens body 3 become closer in proximity during the compression. Support loops 6 and 7 are held against the ciliary sulcus 52. The lens body is positioned so that it does not contact iris 56 of the eye. The positioning of the lens body is effected by virtue of the sloped portions 23 and 24 which position the lens body posteriorly of the iris 56 as clearly shown in FIG. 5. It will be observed that the lens body 2 is positioned with its spherical surface 5 facing forwardly, which is the preferred arrangement. The lens body 2 is held in place by support loops 6 and 7 without the need for additional sutures by means of the outward radial force applied by loops 6 and 7 at contact portions 13, 15 and 16 against the ciliary sulcus 52.

Figure 6:
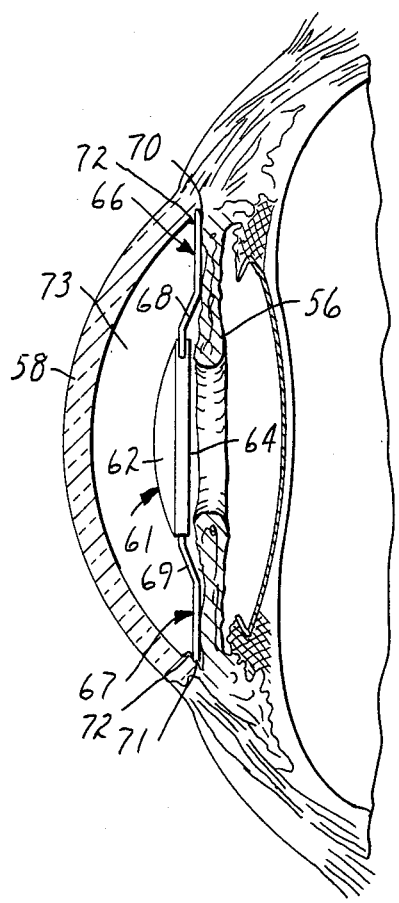
FIG. 6 is a bisected sectional view of the eye with an alternative embodiment of the lens of the invention implanted in the anterior chamber.

Referring now to FIG. 6, it is also contemplated, in accordance with another embodiment of the present invention, to utilize the intraocular lens of the present invention for implantation anteriorly of the iris. As shown in FIG. 6, lens 61 includes a lens body 62, and first and second support loops 66 and 67. The legs of support loops 66 and 67 have sloped portions 68 and 69 which are inclined somewhat posteriorly to lens body 62. Sloped portions 68 and 69 are inclined so that transverse portion 70 lies in the same plane with transverse portion 71. The plane of transverse portions 70 and 71 is substantially parallel to the posterior surface 64 of the lens body 62. The degree of inclination of sloped portions 68 and 69 is such that the perpendicular distance from the plane of transverse portions 70 and 71 to the posterior surface 64 of the lens body is between about 0.1 and 1.5 mm, preferably between about 0.3 and 1.0 mm, and most preferably about 0.6 mm.

The entire lens 61 is positioned anteriorly of the iris 56, with transverse portions 70 and 71 seated in upper and lower regions, respectively, of the groove behind the scleral spur 72. The lens body 62 is held in place by support loops 66 and 67 without the need for additional sutures by means of the outward radial force applied by loops 66 and 67 at the contact portions (not shown) on transverse portions 70 and 71 against the scleral spur 72. The lens body 62 resides in the anterior chamber 73, in front of the iris 56 and behind the cornea 58.

It is important to note that the lens 61 may be successfully implanted in the posterior chamber of the eye, as well as the anterior chamber. This may be accomplished simply by turning the lens in FIG. 6 around so that the lens body 62 lies posteriorly to, the transverse portions 70 and 71 and so that the posterior surface 64 of the lens body 62 faces forwardly, an arrangement that is not normally employed with lens implants; but which provides the same optical effect as the normal orientation in which the spherical surface 65 faces fowardly as shown in FIG. 6. The lens 61 may then be positioned in the posterior chamber, posteriorly to the iris, by positioning transverse portions 70 and 71 of loops 66 and 67 against the ciliary sulcus. The lens body 62 will then be held in place by support loops 66 and 67 without the need for additional sutures.

Figure 7:
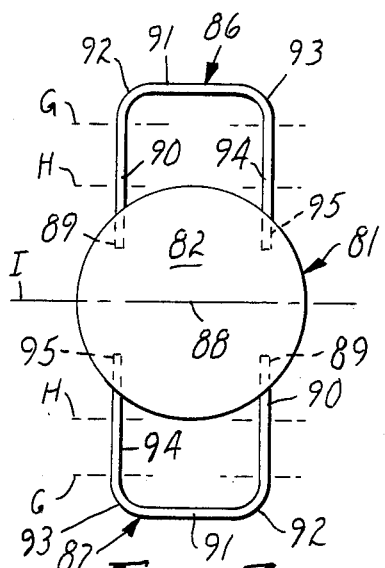
FIGS. 7 and 8 are front elevation views of lenses of the prior art.

The lens of the present invention, due to the particular construction of the asymmetric support loop, has improved stability when positioned in the eye. Additionally the particular loop construction affords a lens which exerts less force when compressed than do vaulted loop intraocular lenses of the prior art. Reference is made in the following discussion to two intraocular lenses of the prior art, illustrated in FIGS. 7 and 8. Both of these prior art lenses have support loops which contain sloped or vaulted portions. Referring to FIG. 7, an elevational view of a vaulted two-loop lens 81 is shown. The lens of FIG. 7 includes a lens body 82, which has a convex anterior surface and a flat posterior surface, and identical symmetric support loops 86 and 87 made of a polymeric material. Loops 86 and 87, have end portions 89 and 95 attached to lens body 82, and columnar leg portions 90 and 94 which extend from end portions 89 and 95, respectively. Loops 86 and 87 also have transverse portion 91 which extends transversely between leg portions 90 and 94 and contains a first contact portion 92 and second contact portion 93. Loops 86 and 87 contain sloped portions lying between imaginary lines G and H, which are inclined somewhat posteriorly to lens body 82. These sloped portions are inclined such that transverse portion 91 lies in a plane parallel to the posterior of the lens body 82. Imaginary lines G and H are parallel to an imaginary line I which is perpendicular to both columnar leg portions 90 and 94, and intersects and is perpendicular to the geometric axis 88 of the lens body 82. The lens illustrated by FIG. 7 is commercially available as the "Leiske ® Physioflex ® Style 10 Anterior Chamber Lens" from Surgidev Corporation.

Figure 8:
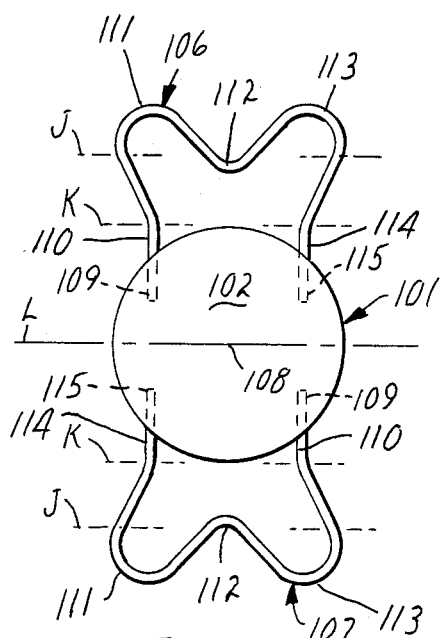

Referring to FIG. 8, an elevational view of another vaulted loop lens of the prior art is shown. The lens 101 includes a lens body 102 which is identical to the lens body 82, and identical symmetric support loops 106 and 107, made of polymeric material. The loops 106 and 107 have end portions 109 and 115 attached to the lens body, and columnar leg portions 110 and 114 which extend from end portions 109 and 115, respectively. Connecting legs 110 and 114 is a transverse portion comprising a first contact foot portion 111 and a second contact foot portion 113 with each foot portion being of arcuate configuration having a center of curvature between it and the lens body 102, as is apparent from an inspection of FIG. 8. Contact portions 111 and 113 are connected by an inwardly extending oppositely curved arcuate connector portion 112 which has a center of curvature positioned outwardly from itself with respect to the lens body 102.

Loops 106 and 107 also contain sloped portions lying between imaginary lines J and K, which are inclined somewhat posteriorly to lens body 102. These sloped portions are inclined such that portions 111, 112 and 113 lie in a plane which is substantially parallel to the posterior surface of the lens body 102. Imaginary lines J and K are parallel to an imaginary line L which is perpendicular to the columnar leg portions 110 and 114 and intersects the geometric axis 108 of the lens body 102. The lens illustrated by FIG. 8 is commercially available as the "Liteflex ® Style 70 Anterior Chamber Intraocular Lens" from McGhan/3M.

Projection of the lens body into a plane parallel to its original position, is generally observed when the support loops of an intraocular lens are compressed. The loops are subject to compression during implantation, and after implantation during normal flexing of the eye. It is desirable to reduce the degree of projection of the lens body, particularly if the lens is to be used in the anterior chamber, since projection of the lens body may result in the lens touching the cornea which can cause the death of endothelial cells and ultimately loss of the cornea. The lenses of the present invention have a reduced tendency to project when subjected to loop compression. This reduced tendency to project is illustrated by the graph in FIG. 9, which contains projection versus compression data for lenses of the prior art and lenses of the instant invention. Curves M and N illustrate compression versus projection for lenses of the the prior art. Curve M relates to the intraocular lens of the prior art which is illustrated by FIG. 7. Curve N relates to the intraocular lens of the prior art which is illustrated by FIG. 8. Curve O illustrates compression versus projection for the lens illustrated in FIG. 1, and Curve P illustrates compression versus projection for the lens illustrated in FIG. 3.

Figure 9:
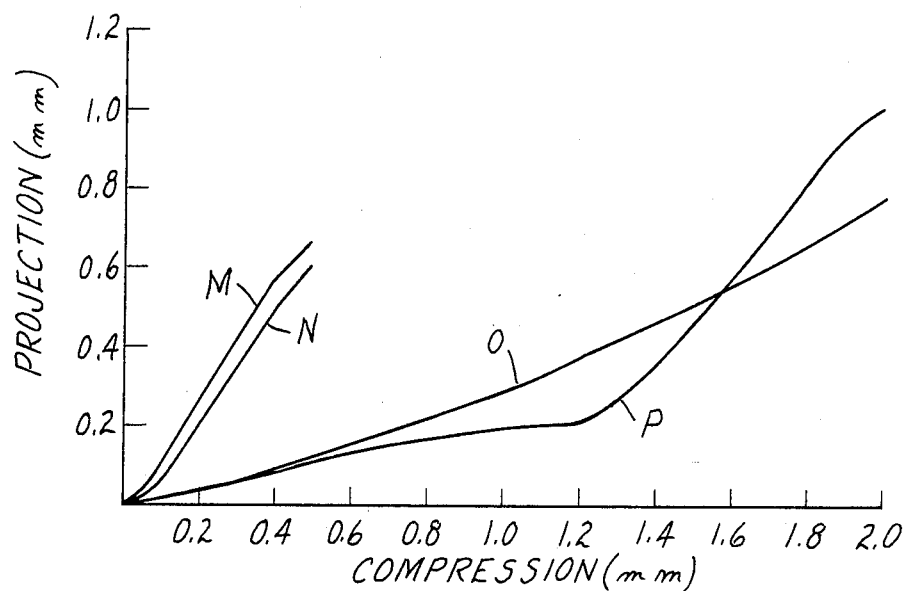
FIG. 9 is a graphic presentation comparing lens projection versus loop compression for lenses of the invention and lenses of the prior art.

The data in FIG. 9 was obtained by placing each lens between two nylon blocks, which have been machined to approximate the average curvature of the eye. One nylon block is placed so that its curved portion lies adjacent the contact portions of the first support loop, and the other is placed so that its curved portion is adjacent the contact portions of the second support loop. This assembly is mounted in a Jones and Lamson optical comparator, Model FC-14. With the lens in place the two blocks are brought closer to one another in 0.1 mm increments using the micrometer dial on the optical comparator. After each 0.1 mm increment of compression, the distance that the posterior surface of the lens body has moved from its original relaxed loop position is measured.

As is shown in FIG. 9, the lenses of the present invention (Curves O and P) have a reduced tendency to project as compared with vaulted loop lenses of the prior art (Curves M and N). The lenses of the present invention can be compressed at least about 1.5 mm without seriously affecting the performance of the lens. The lenses of FIGS. 7 and 8 cannot be compressed to this degree without resulting in an unacceptable amount of lens projection.

It is generally observed that when the support loops of an intraocular lens are subjected to compression they exert a force in a direction opposite to the force of compression. It has been found that the lenses of the invention exert less force in the direction opposite the force of compression than do the closed loop vaulted lenses of the prior art. Thus, the lenses of this invention when implanted in the eye have a reduced tendency to injure adjacent eye tissue if the loops are subjected to any loop compressive forces while in the eye. The graph of FIG. 10 contains compression versus force data for both lenses of the instant invention and the prior art lenses illustrated by FIGS. 7 and 8. Curve Q relates to the lens of FIG. 7, Curve R relates to the lens of FIG. 8, Curve S relates to the lens of FIG. 3, and Curve T relates to the lens of FIG. 1. The data graphed in FIG. 10 was obtained by compressing the loops of the lens using the procedure described hereinabove. The lens was coupled to a Mettler Model PC 180 force compensation scale which measured the force exerted by the loops. A force reading was taken after each 0.1 mm increment of compression.

Figure 10:
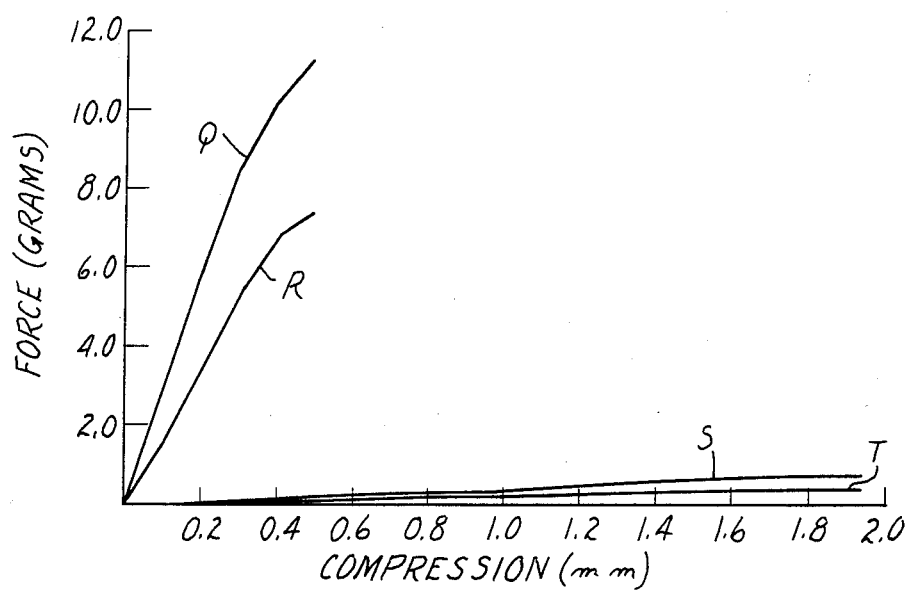
FIG. 10 is a graphic presentation comparing force versus loop compression for lenses of the invention and lenses of the prior art.

As is shown in FIG. 10, the lenses of the instant invention (Curves S and T) exert less force in a direction opposite to the force of compression than do vaulted closed loop lens of the prior art (Curves Q and R), when subjected to the same degree of loop compression. The lenses of this invention can be subjected to at least about 2.0 mm of compression before they exert an unacceptable degree of force. This same degree of compression in the lenses of FIGS. 7 and 8 would result in the loops of these lenses exerting a totally unacceptable degree of force.

In summary, the lenses of the instant invention have improved properties over vaulted closed loop lens of the prior art in that they can accomodate greater degrees of loop compression while maintaining the lens body in a relatively stable position and without producing excessive forces which could result in damage to eye tissues when the intraocular lens is implanted in the eye.

Numerous modifications of the preferred embodiments of the lens of the invention will undoubtedly occur to those of skill in the art. It should be understood that the scope of the invention is not limited to the preferred embodiments but is limited solely by the appended claims.

What is claimed is:

1. An intraocular lens comprising a lens body; first and second support members extending from the lens body for engaging adjacent portions of the anterior or posterior chamber of the eye, at least one of said support members comprising a resilient spring-like asymmetric support loop extending outwardly from the periphery of said lens body, said support loop having first and second end portions attached to the lens body at first and second attachment locations, first and second legs extending from said first and second end portions, respectively, each of said legs containing a sloped portion with the sloped portion of said first leg being nearly equal in length to the sloped portion of said second leg; and a transverse portion extending generally transversely relative to said first and second legs and with opposite sides being respectively unitarily connected to outer ends of said first and second legs and having at least one outer contact portion dimensioned and shaped to engage adjacent portions of the anterior or posterior chambers of the eye with an outward radial force when positioned therein so that at least one of said outer contact portions is deflected inwardly from the normal relaxed position by the adjacent portion of the eye to provide support for said lens body, said transverse portion lying in a plane which is spaced apart from but substantially parallel to the plane of said lens body.

2. The intraocular lens of claim 1 wherein said sloped portions of said first and second legs differ in length by no more than about 30 percent.

3. The intraocular lens of claim 1 wherein said sloped portions have a degree of inclination such that the perpendicular distance from the plane of said transverse portion to the plane of said lens body is between about 0.3 and 1.0 mm.

4. The intraocular lens of claim 1 wherein said first leg has a columnar support portion and said second leg has a cantilever support portion.

5. The intraocular lens of claim 4 wherein said sloped portions of said first and second legs lie between two imaginary lines which are non-parallel to a line which is perpendicular to said columnar leg.

6. The lens of claim 1 wherein said first leg and said second leg extend outwardly from said first and second end portions in substantially opposite directions.

7. The intraocular lens of claim 1 wherein said transverse portion is curved outwardly away from the periphery of said lens body.

8. The intraocular lens of claim 1 wherein said transverse portion comprises two or more linear segments, and said outer contact portions are located at the intersection of said transverse portion with said first and second legs and at the intersection of said linear segments of said transverse portion.

9. The intraocular lens of claim 1 wherein said first and second attachment locations are both on one side of a diameter of said lens body.

10. The intraocular lens of claim 1 wherein said support members further include a second resilient spring-like support loop which is identical to said first-mentioned support loop, said support loops being positioned on said lens body in symmetrical relation to each other.

11. The intraocular lens of claim 10 wherein said transverse portions of said first and second support loops are positioned in a common plane which is spaced apart from but substantially parallel to the plane of said lens body.

12. The intraocular lens of claim 10 wherein said sloped portions of said first and second support loops are inclined anteriorly to said lens body, and wherein said lens is particularly suitable for implantation into the posterior chamber of said human eye.

13. The intraocular lens of claim 10 wherein said sloped portions of said first and second support loops are inclined posteriorly to said lens body, and wherein said lens is particularly suitable for implantation into the anterior chamber of said human eye.

14. An intraocular lens comprising a lens body; first and second support members extending from the lens body for engaging adjacent portions of the anterior or posterior chamber of the eye, at least one of said support members comprising a resilient spring-like asymmetric support loop extending outwardly from the periphery of said lens body, said support loop having first and second end portions attached to the lens body at first and second attachment locations, first and second leg portions extending from said first and second end portions, respectively, each of said leg portions containing a sloped portion with the sloped portion of said first leg being nearly equal in length to the sloped portion of said second leg; and a transverse portion comprising two or more linear segments extending generally transversely relative to said first and second leg portions and with opposite sides being respectively unitarily connected to outer ends of said first and second leg portions and having three distinct outer contact portions located at the intersection of said transverse portion with said first and second legs and at the intersection of said linear segments of said transverse portion, said outer contact portion dimensioned and shaped to engage adjacent portions of the anterior or posterior chambers of the eye with an outward radial force when positioned therein so that at least one of said outer contact portions is deflected inwardly from the normal relaxed position by the adjacent portion of the eye to provide support for said lens body, said transverse portion lying in a plane which is spaced apart from but substantially parallel to the plane of said lens body.

* * * * *